(12) United States Patent
Dalton

(10) Patent No.: US 7,794,445 B2
(45) Date of Patent: Sep. 14, 2010

(54) NEEDLE SAFETY AND PROTECTION DEVICE

(76) Inventor: Michael J. Dalton, 7350 N. Ridgeway, Skokie, IL (US) 60076

( * ) Notice: Subject to any disclaimer, the term of this patent is extended or adjusted under 35 U.S.C. 154(b) by 962 days.

(21) Appl. No.: 11/049,488

(22) Filed: Feb. 2, 2005

(65) Prior Publication Data

US 2005/0131384 A1  Jun. 16, 2005

Related U.S. Application Data

(63) Continuation-in-part of application No. 10/407,486, filed on Apr. 4, 2003, now Pat. No. 6,884,224.

(51) Int. Cl.
*A61M 31/00* (2006.01)
(52) U.S. Cl. ...................... 604/506; 604/263
(58) Field of Classification Search ............... 600/573, 600/575–579, 581; 604/110, 115, 117, 162, 604/164.08, 263, 192–199, 19, 93.01, 180, 604/164.01, 264, 272, 500, 506; 606/181–183
See application file for complete search history.

(56) References Cited

U.S. PATENT DOCUMENTS

| | | | | |
|---|---|---|---|---|
| 4,850,961 A | * | 7/1989 | Wanderer et al. ........... 604/508 |
| 5,120,321 A | * | 6/1992 | Oksman et al. ............. 604/198 |
| 5,364,370 A | * | 11/1994 | Szerlip et al. .............. 604/192 |
| 5,681,295 A | * | 10/1997 | Gyure et al. ................ 604/263 |
| 5,951,522 A | * | 9/1999 | Rosato et al. .............. 604/177 |
| 5,984,899 A | * | 11/1999 | D'Alessio et al. .......... 604/198 |
| 6,261,264 B1 | * | 7/2001 | Tamaro ...................... 604/198 |
| 6,884,224 B2 | * | 4/2005 | Dalton ....................... 600/573 |
| 2002/0055711 A1 | * | 5/2002 | Lavi et al. .................. 604/110 |

* cited by examiner

*Primary Examiner*—Kevin C Sirmons
*Assistant Examiner*—Michael J Anderson

(57) ABSTRACT

A fluid delivery device for delivering fluid to a patient includes a fluid delivery tube, a needle in communication with the fluid delivery tube, a base connected adjacent a distal portion of the fluid delivery tube and a flexible shield connected at one end to the base. The shield includes an adhesive portion located on an outer surface, wherein in an insertion configuration the needle fits through a shield aperture and the adhesive portion contacts a target skin region, and when in a protection configuration a needle tip contacts a portion of an inner surface of the shield spaced apart from the shield aperture when the fluid delivery device is removed from the skin region.

20 Claims, 9 Drawing Sheets

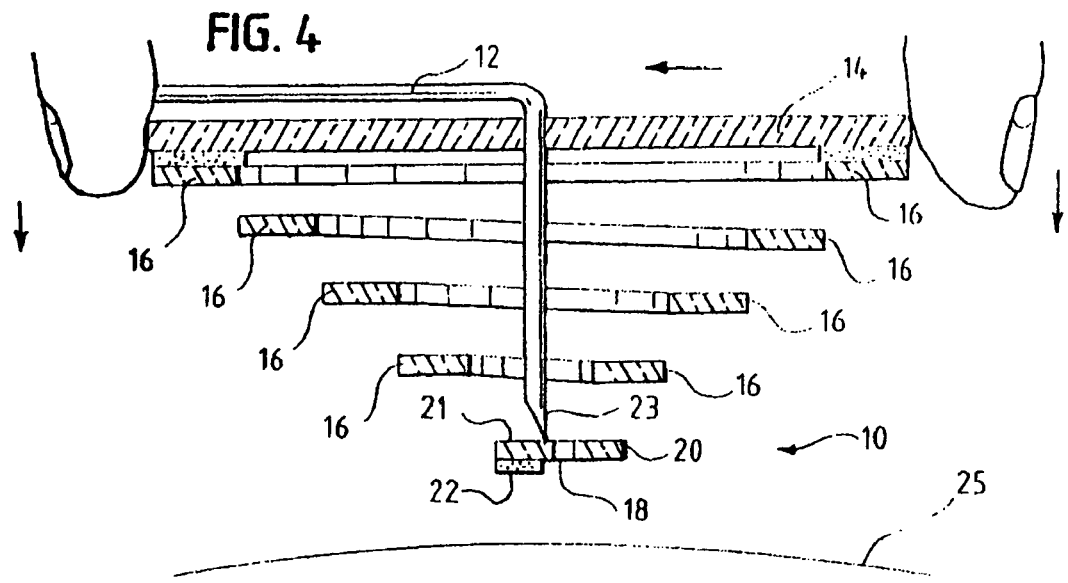
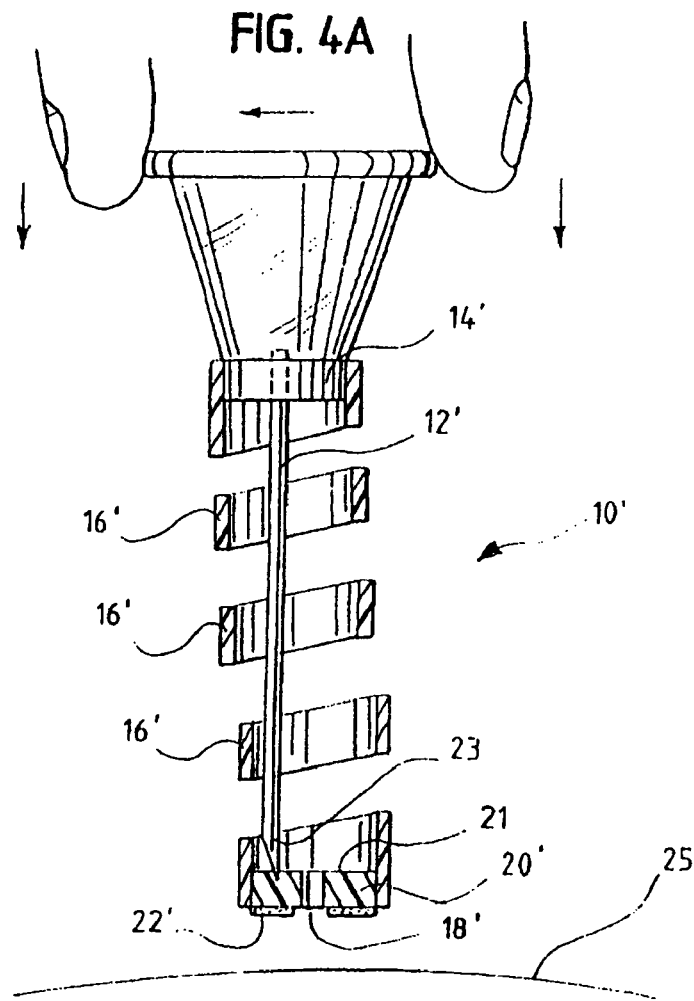

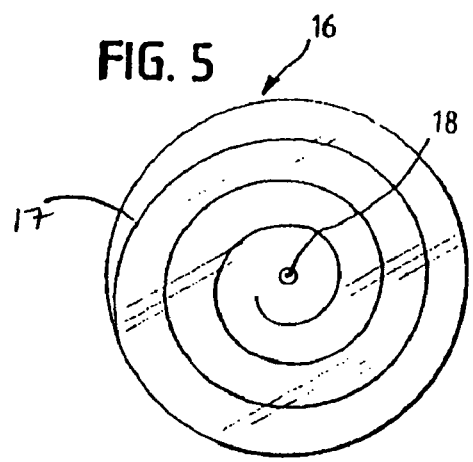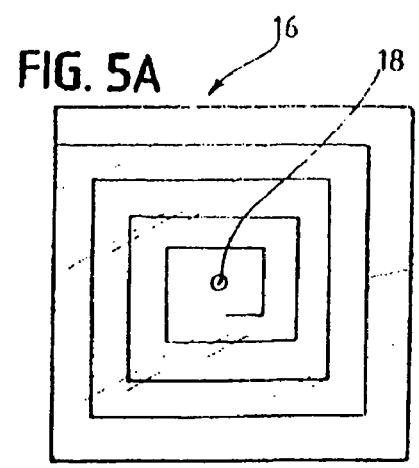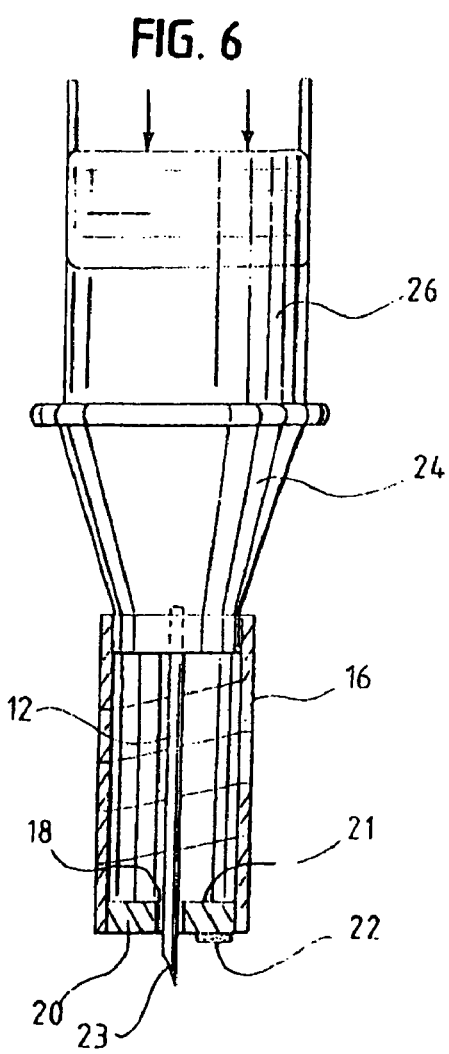

FIG. 11    200
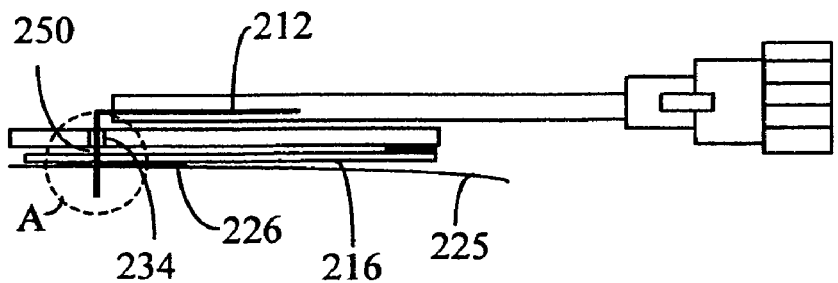
FIG. 12    200
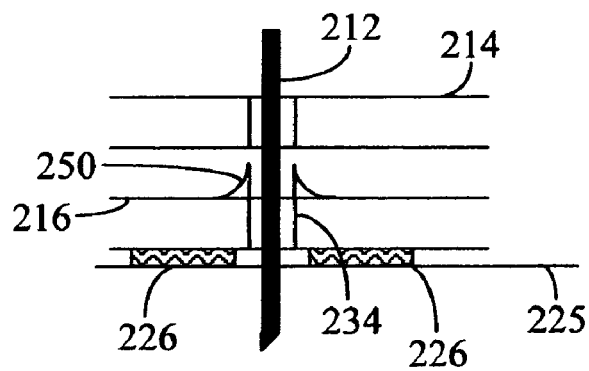
FIG. 13    200
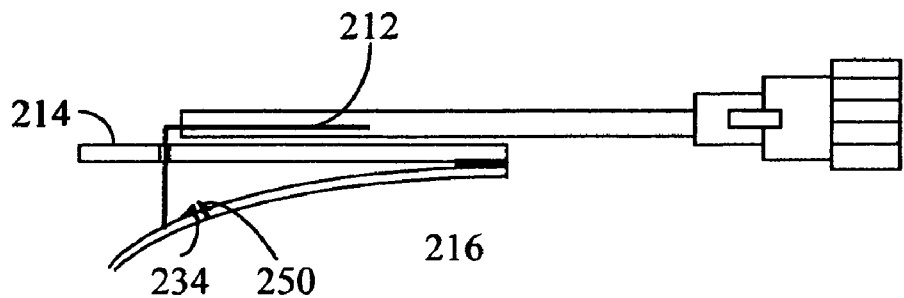

NEEDLE SAFETY AND PROTECTION DEVICE

RELATED APPLICATIONS

The present application is a continuation in part of U.S. patent application Ser. No. 10/407,486, "Needle Safety Protection Device", filed Apr. 4, 2003, now issued as U.S. Pat. No. 6,884,224, by Michael J. Dalton, the entirety of which is incorporated herein by reference.

TECHNICAL FIELD

The present invention is an improved device for protecting users from needle sticks by automatically capping the used needle the instant the needle is withdrawn from the patient to protect the user against infection risks.

BACKGROUND OF THE INVENTION

Needles are used in the medical industry to deliver medications or to draw blood for diagnosis. United States health authorities estimate that some 600,000 to 800,000 accidental needle stick injuries occur every year. There are roughly 8,000,000 healthcare workers in the United States who are at risk of being stuck with a needle that is contaminated with HIV, hepatitis, herpes, tuberculosis, fungi and a full range of other infectious microorganisms.

The purpose of this invention is to address the problem of transmission of diseases as a result of user contact with used needles. Although currently there exist various needle protection devices, most require the user to take an affirmative step thereby causing potential risk of contact with the needle. Furthermore, there are not any needle protection devices that address the issues faced by subcutaneous needles.

What is needed, therefore, is a needle protection device that overcomes these and other disadvantages.

SUMMARY OF THE INVENTION

A first aspect of the present invention provides a fluid delivery device for delivering fluid to a patient. The fluid delivery device comprises a fluid delivery tube, a needle received within a distal portion of the fluid delivery tube, a base connected adjacent a distal portion of the fluid delivery tube and a shield connected at one end to the base. The shield has an adhesive portion located on an outer surface, wherein in an insertion configuration the needle fits through a shield aperture and the adhesive portion contacts a target skin region, and wherein in a protection configuration a needle tip contacts a portion of an inner surface of the shield spaced apart from the shield aperture.

A second aspect of the present invention provides a fluid delivery device. The fluid delivery device comprises a fluid delivery tube, a needle including a first portion received within a distal portion of the tube and a second portion positioned at an angle to the first portion, a base connected adjacent a distal portion of the tube and shield means for adhering to a target skin region during delivery and shielding a tip of the second portion of the needle during removal.

A third aspect of the present invention provides a method for delivering fluid to a patient. The method comprises applying an adhesive portion of a fluid delivery device to a target skin region, transferring fluid through a needle of the device, and removing a base portion of the device while simultaneously flexing a shield portion of the device to secure a tip of the needle against an inner portion of the shield portion.

The foregoing and other features and advantages of the invention will become further apparent from the following detailed description of the presently preferred embodiments, read in conjunction with the accompanying drawings. The figures are not drawn to scale. The detailed description and drawings are merely illustrative of the invention, rather than limiting the scope of the invention being defined by the appended claims and equivalents thereof.

BRIEF DESCRIPTION OF THE DRAWINGS

FIG. 4 is a cut away side view of the needle protection device with a completely withdrawn right angle needle and the shield device has released from the patient's skin whereby the needle point has become fixed into the shield device;

FIG. 4A is a cut away side view of the needle protection device with a completely withdrawn straight needle and the shield device has released from the patient's skin whereby the needle point has become fixed into the shield device;

FIGS. 5 and 5A are top views of the spiral type cut shield according to the invention;

FIG. 6 is a cut away side view of the needle protection device mounted to a cone according to the invention;

FIG. 11 is a side view of another embodiment of a needle protection device in an insertion configuration according to the present invention;

FIG. 12 is a detailed view of a portion of the needle protection device illustrated in FIG. 11;

FIG. 13 is a side view of the needle protection device of FIG. 11 in a protection configuration according to the present invention.

DETAILED DESCRIPTION

Figure 1:
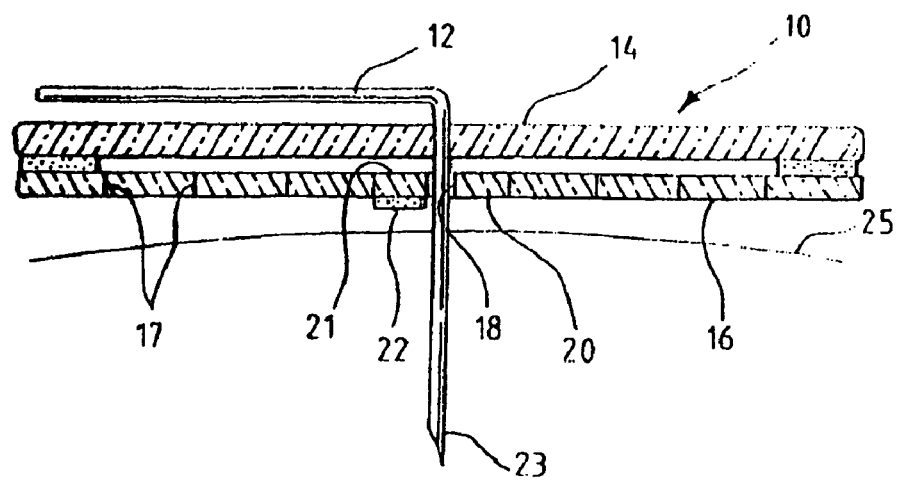
FIG. 1 is a cut away side view of the needle protection device with a right angle needle inserted in skin with the shield device in a "relaxed" position according to the invention.
Figure 1A:
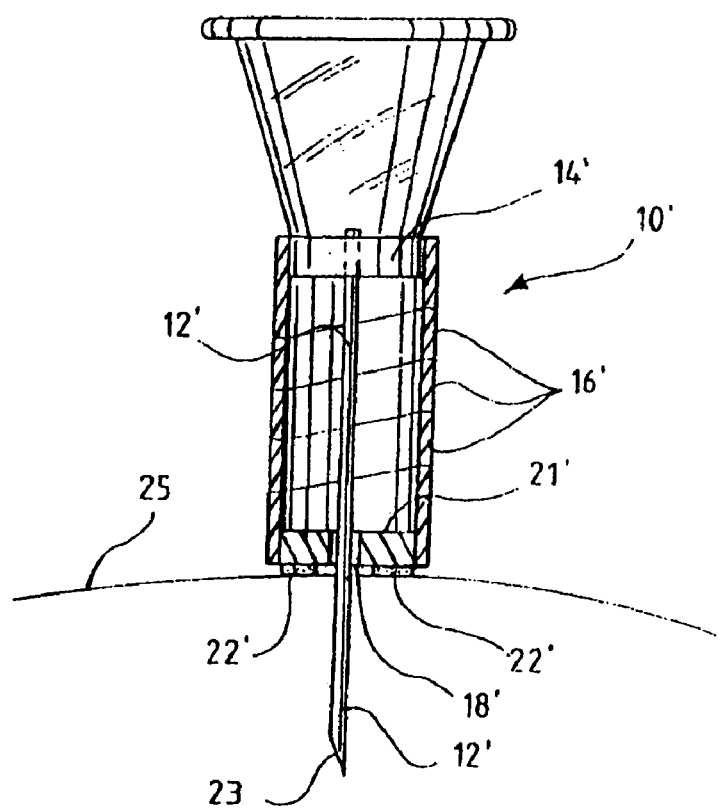
FIG. 1A is a cut away side view of the needle protection device with a straight needle inserted in skin with the shield device in a "relaxed" position according to the invention.

The needle safety and protection device 10 and 10' is attached to a conventional medical needle 12 and 12', and comprises a base 14 and 14', and a shield 16 and 16', as shown in FIGS. 1 and 1A. The base 14 and 14' is made of a semi-rigid polymeric material and is mounted on the needle 12 and 12' or on a support for the needle, at a distance sufficient to allow the needle 12 and 12' to enter human skin and perform its function appropriately.

Shield 16 and 16' is attached to the base 14 and 14' at the outer circumference of the base 14 and 14'. The shield 16 and 16' is attached to the base by way of adhesive, heat seal, or any suitable method, and is made of a semi-rigid polymeric. The shield 16 and 16' has a spiral type cut 17 and 17', as shown in FIGS. 5 and 5A, to allow for extension of the shield 16 and 16' away from the base 14 and 14'. The shield 16 and 16' has a aperture 18 and 18' in its face 20 and 20'. The aperture 18 and 18' is slightly off-center on the face or surface 20 and 20' to prevent the tip 23 of the needle 12 and 12' from injuring the patient or a user, and the aperture 18 is large enough for the needle 12 and 12' to pass through. An adhesive 22 and 22' is attached to an outer portion of the face 20 and 20' of the shield 16 and 16' in a manner where it does not impede the movement of the needle 12 and 12' through the aperture 18 and 18' on the face 20 and 20' of the shield 16 and 16'. As is shown in FIGS. 1 and 1A, when the needle 12 and 12' is inserted into a patient, through the skin 25 shield 16 and 16' is in a "relaxed" or flat position wherein the adhesive 22 and 22' contacts the skin 25 of the patient. The adhesive 22 and 22' temporarily holds the face 20 and 20' of the shield 16 and 16' to the patient's skin.

Figure 2:
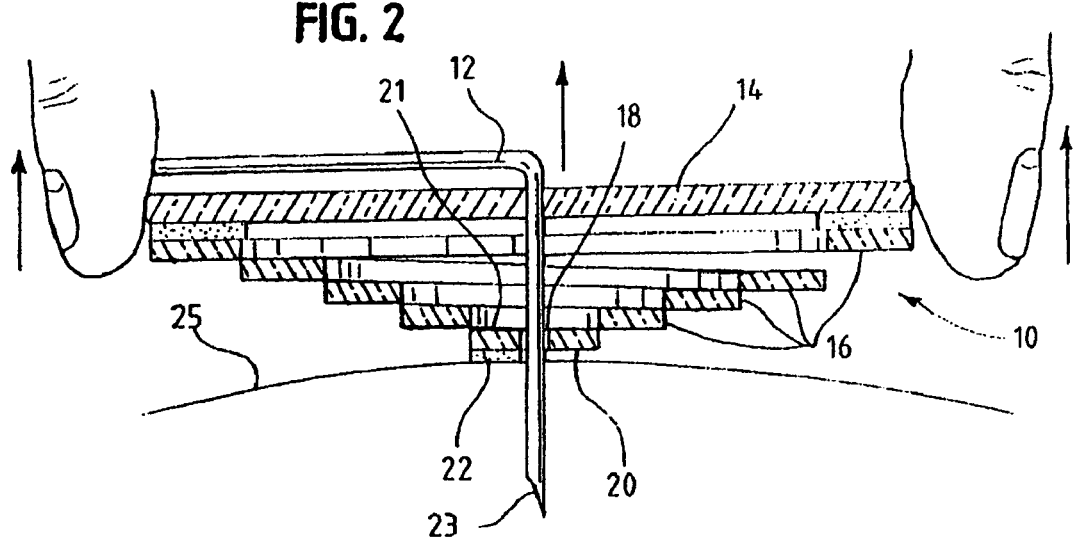
FIG. 2 is a cut away side view of the needle protection device as the right angle needle is being withdrawn from the skin and an adhesive patch remains in contact with the skin whereby extending the shield according to the invention.
Figure 2A:
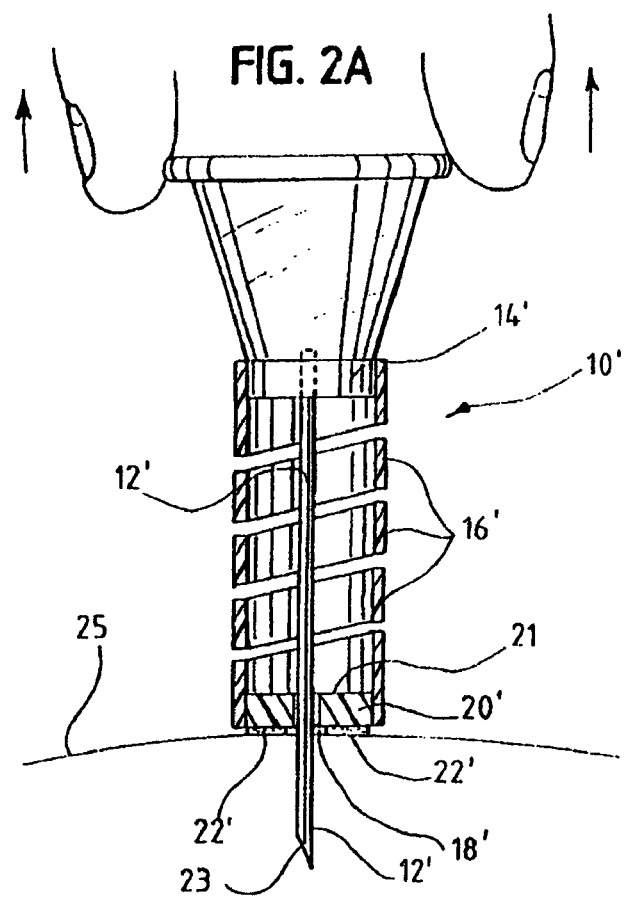
FIG. 2A is a cut away side view of the needle protection device as the straight needle is being withdrawn from the skin and an adhesive patch remains in contact with the skin whereby extending the shield according to the invention.

As is shown in FIGS. 2 and 2A, as the needle 12 and 12' is withdrawn from the skin 25, the adhesive 22 and 22' remains in contact with the patient's skin and the tension force in shield 16 and 16' increases. The tensile force created by the withdrawal of the needle 12 and 12' is insufficient to break the force of the adhesive 22 and 22' holding shield 16 and 16' to the skin 25. This compels the spiral type cut shield 16 and 16' to extend into a protective cone shape along the length of the needle 12 and 12'. When the needle 12 and 12' is fully extended protective shield 16 and 16'.

Figure 3:
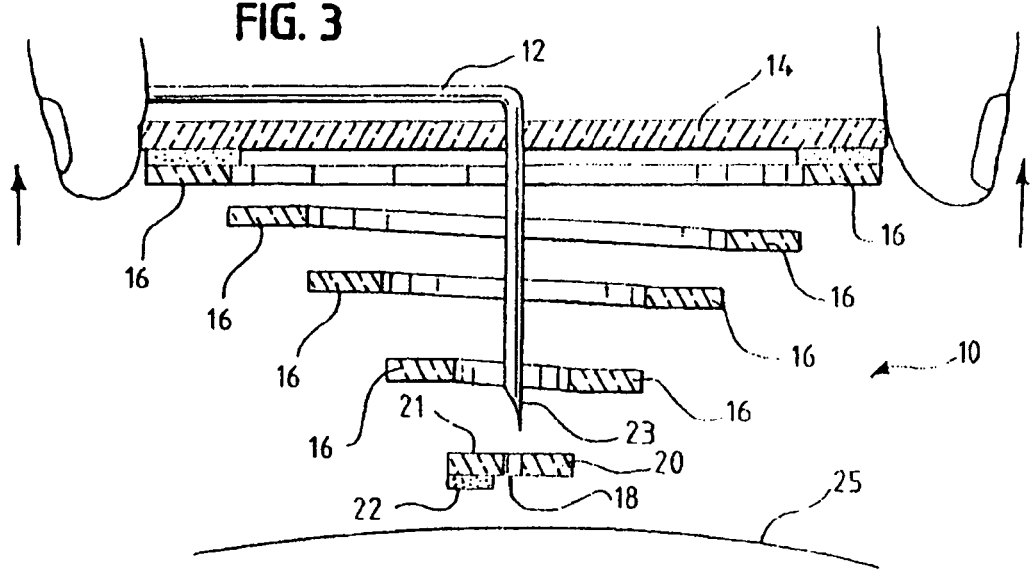
FIG. 3 is a cut away side view of the needle protection device with a right angle needle being withdrawn from the skin and the shield device is in an extended position according to the invention.
Figure 3A:
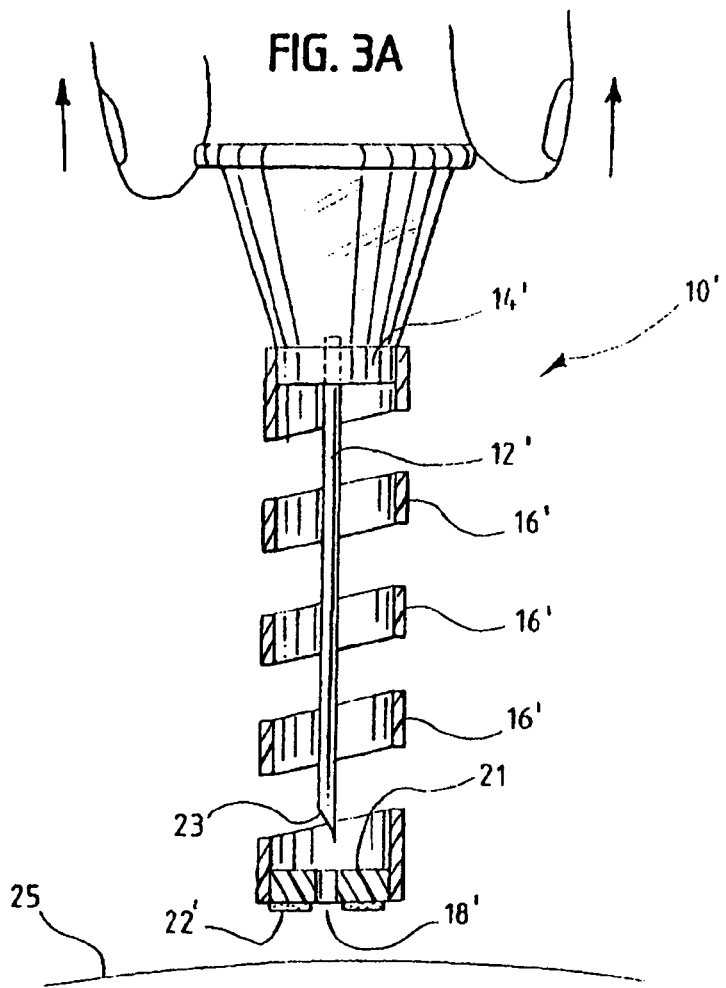
FIG. 3A is a cut away side view of the needle protection device with a straight needle being withdrawn from the skin and the shield device is in an extended position according to the invention.

As is shown in FIGS. 3 and 3A, when the needle 12 and 12' is completely withdrawn from the patient, the adhesive 22 and 22' releases from the patient's skin under the increase in tensile force created by the spiral cone formation of shield 16 and 16', and without affirmative action by a user. The shield 16 and 16' then begins to recoil back to the base 14 and 14'. However, as shown in FIGS. 4 and 4A, because the aperture 18 and 18' is slightly off center on the face 20 and 20' of the shield 16 and 16', the tip 23 of the needle 12 and 12' engages a portion of the inside face or surface 21 and 21' of the shield 16 and 16', and stops the shield 16 and 16' from recoiling into a fully relaxed position. Because the tip 23 of the needle 12 and 12' cannot again slide through the aperture 18 and 18', the face 20 and 20' of the shield 16 and 16' protects a user from being stuck by needle 12 and 12'.

In another embodiment of the invention, the shield 16 is attached to a cone 24, which is then fastened to a syringe 26, as shown in FIG. 6. The shield 16 operates the same way as described above whether it is attached to a needle 12 a needle housing or cone 24.

FIGS. 7 to 10, in which like elements share like reference numbers, illustrate another embodiment of a needle protection device 100. FIGS. 7 to 10 illustrate a needle protection device having a shield that adheres to the patient's skin when the needle is inserted. When the needle is withdrawn a base separates from the adhered shield and the needle slips from an aperture in the shield. When the adhesive releases from the patient's skin the needle tip catches on an inside surface of the shield and is prevented from slipping through the shield aperture.

Figure 7:
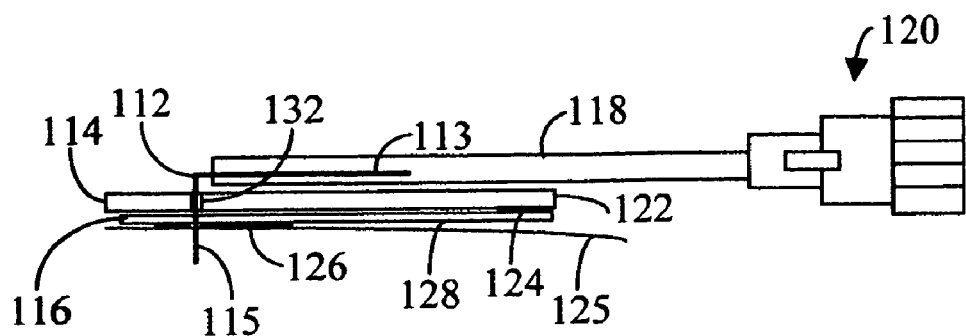
FIG. 7 is a side view of another embodiment of a needle protection device in an insertion configuration according to the present invention.
Figure 8:
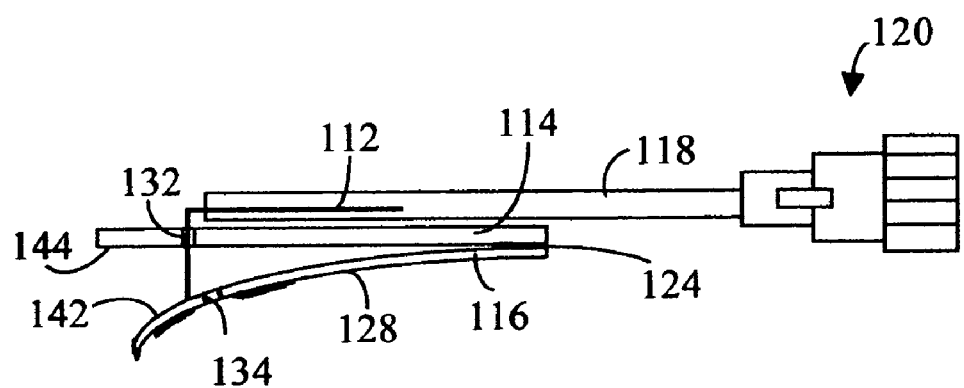
FIG. 8 is a side view of the needle protection device of FIG. 7 in a protection configuration according to the present invention.

FIG. 7 is a side view of the needle protection device 100 in a relaxed configuration and FIG. 8 is a side view of the needle protection device 100 in a protection configuration. Needle protection device 100 includes needle 112, base 114 and shield 116. The inner hollow portion of needle 112 is in communication with the inner portion of fluid delivery tube 118 as is known in the art. In one embodiment, needle 112 is a hollow needle having a first portion 113 received in the fluid delivery tube and a second portion 115 positioned at an angle to the first portion 113. The second portion 115 includes a needle tip 140 for insertion into a patient. In one embodiment, needle 112 is a right angle subcutaneous needle as are known in the art. A Luer fitting 120 may be attached at an end of the fluid delivery tube 118 opposite the needle 112 as is known in the art for connecting the fluid supply to the needle protection device 100. Those of skill in the art will recognize that the invention may be practiced with needles other than right angle subcutaneous needles such as, for example, straight needles or curved needles. Needle 112 may also vary in length and gauge as desired for a particular use.

The base 114 is mounted on the needle 112 or on a support for the needle, at a distance sufficient to allow the needle 112 to enter human skin and perform its function appropriately. Base 114 includes a base aperture 132 through which the needle 112 passes for insertion into the patient's skin. In one embodiment, the base 114 is made of a rigid polymeric material such as, for example, a rigid polyvinylchloride. In one embodiment, the shield 116 is made of a softer (i.e., less rigid) polymeric material than the base to allow for the flexible connection between the base and the shield, as discussed below. The shield material may be, for example, a semi-rigid polyvinylchloride. In another embodiment, the shield is made of the same or similar material as that of the base 114.

Figure 9:
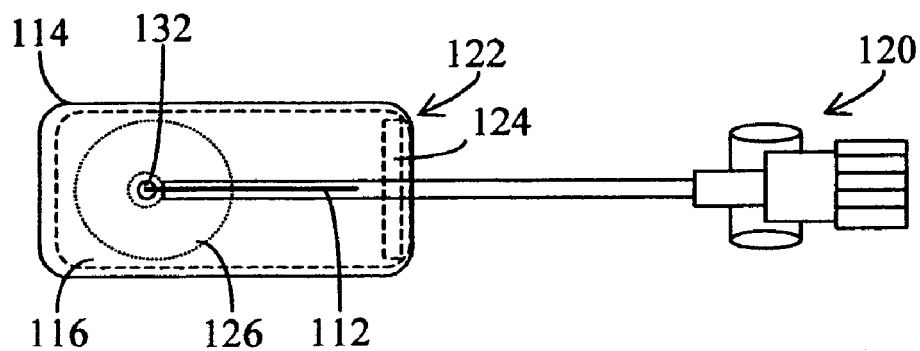
FIG. 9 is a top view of the needle protection device of FIG. 7 according to the present invention.
Figure 10:
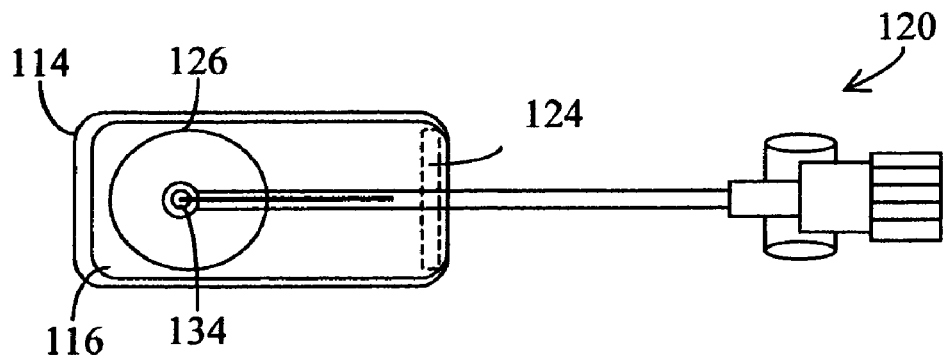
FIG. 10 is a bottom view of the needle protection device of FIG. 7 according to the present invention.

Shield 116 is attached to the base 114 at a proximal portion 122 forming a flexible connection 124 between the shield 116 and the base 114 (see FIGS. 9 and 10). In this detailed description proximal and distal refer to positions in relation to the Luer fitting 120. Shield 116 may be attached to base 114 by any means suitable for forming a flexible connection. In one embodiment, shield 116 is attached to base 114 by adhesive. In other embodiments, shield 116 is attached to base 114 by other means such as, for example, stacking, ultrasonic welding and solvent bonding as are known in the art. In one embodiment, base 114 is flexibly attached to shield 116 by a living hinge as are known in the art. In another embodiment, the shield 116 is attached to base 114 at two or more spaced apart points adjacent proximal end 122. In another embodiment, shield 116 is attached to a portion of fluid delivery tube 118. In this embodiment, fluid delivery tube 118 may include a widened portion near the distal end for attachment of the shield 116.

Shield 116 includes an adhesive layer 126 attached to an outer portion 128 of shield 116. The adhesive layer 126 is attached to the outer portion 128 of the shield 116 in a manner where it does not impede the movement of the needle 112 through a shield aperture 134 of the shield 116. In one embodiment, the adhesive layer 126 has a protective covering that is removed prior to placement on the skin. As shown in FIG. 7, when the needle 112 is inserted into the patient through the skin 125, shield 116 is in a relaxed configuration so that the adhesive layer 126 contacts the skin 125 of the patient. The adhesive 126 temporarily holds outer portion 128 of shield 116 to the patient's skin 125. FIG. 7 also illustrates that when the needle protection device 100 is in the relaxed configuration, base 114 and shield 116 are substantially parallel to one another when the shield 116 adheres to the patient's skin. FIGS. 7, 9 and 10 illustrate that base aperture 132 and shield aperture 134 are substantially aligned to allow passage of the needle 112 through the base 114 and the shield 116 to allow insertion into the patient's skin 125.

FIG. 8 illustrates needle protection device 100 in the protection configuration. The protection configuration is assumed after the needle has been completely withdrawn from the patient's skin. To withdraw the needle from the patient's skin, the practitioner grasps the base 114 and pulls the base 114 and needle 112 in a direction away from the patient's skin. As the base 114 is pulled away from the shield 116, the shield flexes at the connection 124. The shield 116 flexes in relation to the base 114 so that as the inner surface 144 of the base is moved away from the inner surface 142 of the shield 116: the shield 116 and base 114 form an open "V" shape. The adhesive of the adhesive layer 126 causes the shield to remain in contact with the patient's skin until the needle 112 is completely withdrawn from the patient's skin. As the needle tip 140 exits the patient's skin, the needle tip 140 is withdrawn from the shield aperture 134 of shield 116. When the needle 112 is completely withdrawn from the patient and through the shield aperture 134, the adhesive layer 126 releases from the patient's skin 125. Upon release of the shield 116 from the skin, the flexed shield 116 moves toward the inner surface 144 of base 114. The needle tip 140 contacts the inner surface 142 of the shield 116 at a point spaced apart from the shield aperture 134. The needle tip 140 is prevented from entering shield aperture 134 because, once needle 112 exits shield aperture 134, the apertures 132 and 134 are not aligned with respect to the perpendicular axis of the needle, placing the needle tip 140 in a position that engages the inside surface 142 of the shield 116 away from the shield aperture 134. Because the needle tip 140 is prevented from entering shield aperture 134, the protection configuration of the needle protection device 100 is formed and protects a user from being stuck by the used needle 112.

FIGS. 11 to 13, in which like reference numbers refer to like elements, illustrate another embodiment of a needle protection device 200. FIG. 11 illustrates needle protection device 200 in the relaxed configuration and FIG. 13 illustrates needle protection device 200 in the protection configuration. FIG. 12 illustrates a detailed view of the area within circle "A" of FIG. 11.

Needle protection device 200 is substantially similar to that of needle protection device 100, discussed above. Needle protection device 200 further includes surface projection 250 positioned between base 214 and shield 219 when in the relaxed configuration shown in FIG. 11. Surface projection 250 may be an annular projection around shield aperture 234 extending from the inner surface 242 of shield 216. Surface projection 250 provides an additional encumbrance preventing needle tip 240 of needle 212 from entering shield aperture 234 when the adhesive 226 on shield 216 is released from the patient's skin 225.

Figure 14:
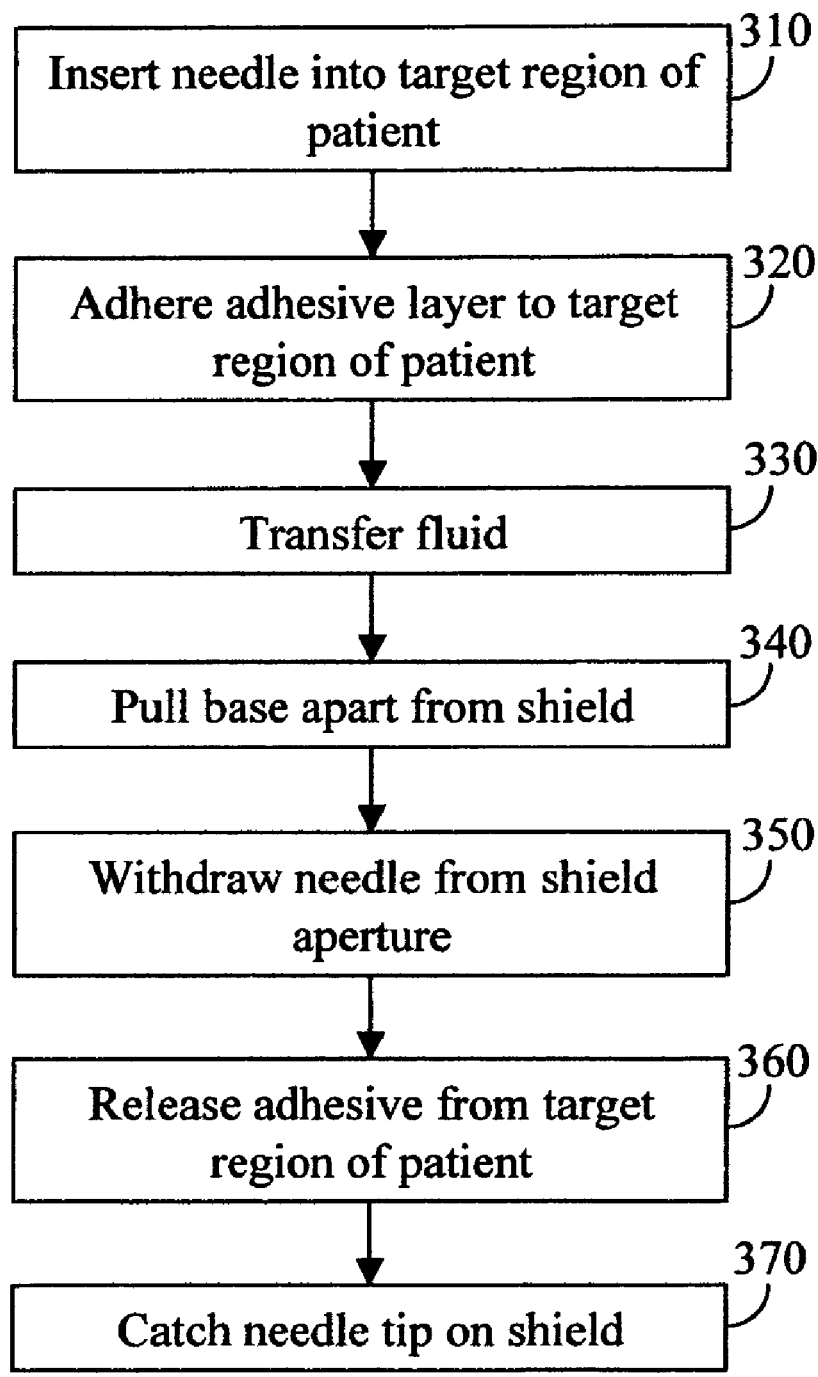
FIG. 14 is a flow chart of a method of using a needle protection device according to the present invention.

FIG. 14 is a flow chart illustrating a method 300 for delivering fluid to a target region of a patient's skin. Method 300 begins when the practitioner inserts a needle of the needle protection device 100 into the target region of a patient's skin (Block 310). The needle protection device is in the relaxed configuration as the needle is inserted into the patient. Next, the practitioner advances the needle, so that the adhesive layer, located on the outside surface of the shield adheres to the patient's skin (Block 320). In one embodiment, the practitioner removes a protective cover from the adhesive layer prior to inserting the needle into the patient's skin in order to expose the adhesive layer. Fluid is then transferred through the needle into the patient, or withdrawn from the patient, as is known in the art (Block 330).

The needle is removed from the patient after the transfer of fluid. To remove the needle, the practitioner grasps the base of the needle protection device and pulls the base away from the skin separating the base from the shield (Block 340). The shield is flexed at the connection by remaining affixed to the patient's skin via the adhesive layer. Continued pulling of the base away from the patient's skin removes the needle from the patient and from the shield aperture (Block 350). Further pulling releases the adhesive layer from the patient's skin (Block 360). Once released, the needle tip catches on the shield (Block 370). Upon release from the skin, the flexed shield moves toward the base. Movement toward the base is stopped when the needle tip contacts the inner surface of the shield at an area spaced apart from the shield aperture. The needle tip is covered by the shield, thereby placing the needle protection device in the protection configuration.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

The invention claimed is:

1. A fluid delivery device comprising:
a fluid delivery tube;
a needle received within a distal portion of the fluid delivery tube;
a planar base mounted to the fluid delivery tube adjacent a distal portion of the fluid delivery tube; and
a planar shield connected at one end to the base with a flexible connection, the shield having an adhesive portion located on an outer surface, wherein in an insertion configuration the planar base and the planar shield are substantially parallel to the fluid delivery tube and the needle fits through a shield aperture and the adhesive portion is adapted to contact a target skin region, and wherein in a protection configuration a needle tip contacts a portion of an inner surface of the planar shield spaced apart from the shield aperture and wherein the planar base remains substantially parallel to the fluid delivery tube.

2. The device of claim 1 wherein the base further comprises a base aperture for receiving the needle.

3. The device of claim 2 wherein the base aperture and the shield aperture are aligned when in the insertion configuration.

4. The device of claim 2 wherein the base aperture and the shield aperture are misaligned when in the protection configuration.

5. The device of claim 1 wherein the shield further includes a surface projection located on the inner surface of the shield and proximate the shield aperture.

6. The device of claim 1 wherein the shield is flexibly connected to the base by an adhesive.

7. The device of claim 1 wherein the shield is flexibly connected to the base by a method chosen from the group of stacking, ultrasonic welding and solvent bonding.

8. The device of claim 1 wherein the base is composed of a rigid polymeric material.

9. The device of claim 1 wherein the shield is composed of a semi-rigid polymeric material.

10. A fluid delivery device comprising:
  a fluid delivery tube;
  a needle including a first portion received within a distal portion of the fluid delivery tube and a second portion positioned at an angle to the first portion;
  a planar base connected adjacent a distal portion of the fluid delivery tube; and
  planar shield means adapted for adhering to a target skin region during delivery and shielding a tip of the second portion of the needle during removal,
  wherein the planar base and the planar shield are substantially parallel to the fluid delivery tube when in an insertion configuration.

11. The device of claim 10 wherein the shield means comprises an adhesive layer located on an outer service of the shield means.

12. The device of claim 10 wherein the base includes an aperture for receiving the needle.

13. The device of claim 10 wherein the shield means includes an aperture for receiving the needle.

14. The device of claim 10 wherein the needle is adapted to be inserted into the target skin region in an insertion configuration.

15. The device of claim 10 wherein the device is adapted to be removed from the target skin region in a protection configuration.

16. The device of claim 11 further comprising a protective covering positioned on the adhesive layer.

17. A method for fluid delivery, the method comprising:
  applying an adhesive portion of a fluid delivery device to a target skin region, the fluid delivery device including a fluid delivery tube, a needle received within a distal portion of the fluid delivery tube, a planar base portion mounted to and parallel with the fluid delivery tube and a planar shield portion directly connected at one end to the base portion;
  transferring fluid through the needle of the device; and
  removing the planar base portion of the device while simultaneously flexing the planar shield portion of the device to secure a tip of the needle against an inner portion of the planar shield portion.

18. The method of claim 17 further comprising:
  inserting the needle of the fluid delivery device into the target skin region prior to applying the adhesive portion.

19. The device of claim 1 wherein the planar shield flexes between an insertion position wherein the needle extends through a base aperture and through a shield aperture and a protection configuration wherein the needle extends through the base aperture and the needle tip contacts an inner surface of the shield.

20. The device of claim 10 wherein the planar shield flexes between an insertion position wherein the needle extends through a base aperture and through a shield aperture and a protection configuration wherein the needle extends through the base aperture and the needle tip contacts an inner surface of the shield.

* * * * *